United States Patent [19]

Rzeszotarski et al.

[11] Patent Number: 4,783,530

[45] Date of Patent: Nov. 8, 1988

[54] 8-ARYLXANTHINES

[75] Inventors: Waclaw J. Rzeszotarski, Millersville; Rickey P. Hicks, Columbia; Ronald H. Erickson, Baltimore, all of Md.

[73] Assignee: Marion Laboratories, Inc., Kansas City, Mo.

[21] Appl. No.: 108,990

[22] Filed: Oct. 1, 1987

Related U.S. Application Data

[63] Continuation-in-part of Ser. No. 931,620, Nov. 13, 1986, abandoned.

[51] Int. Cl.$^4$ .................. C07D 239/36; A61K 31/52
[52] U.S. Cl. ................................ 544/267; 544/272; 544/273; 514/263; 514/265
[58] Field of Search .............. 544/272, 267; 514/263, 514/265

[56] References Cited

U.S. PATENT DOCUMENTS 4,593,095 6/1986 Snyder et al. ................. 544/272

OTHER PUBLICATIONS

Copy provided in parent case.

Primary Examiner—Nicholas S. Rizzo
Attorney, Agent, or Firm—Dewey, Ballantine, Busby, Palmer & Wood

[57] ABSTRACT 1,3-alkylsubstituted-8-(3,4-,3- or 4-substituted phenyl)xanthines and pharmaceutically acceptable salts of such compounds are disclosed. The 3-substituents are hydrogen, dimethylaminomethyl, or 2,3-dihydroxypropyloxy. The 4-substituents are selected from hydroxy, cyano, —NHCON($R_5$)$_2$, —C(=NH)N($R_5$)$_2$, —NH—C(=NH)N($R_5$)$_2$, with each $R_5$ independently being hydrogen or an alkyl group of one to three carbons and provided that when the 3-substituent is hydrogen the 4-substituent is not hydroxy or hydrogen.

The compounds are potent adenosine receptor antagonists having relatively low lipophilicity. The compounds are intended for use as bronchodilators and cardiotonics.

8 Claims, No Drawings

8-ARYLXANTHINES

This application is a continuation-in-part of U.S. Application Ser. No. 06/931,620 filed Nov. 13, 1986, now abandoned.

BACKGROUND OF THE INVENTION (a) Field of the Invention

This invention relates to arylxanthines which are relatively potent adenosine receptor antagonists with enhanced water solubility and beneficial pharmacological activity. The are 1,3-alkyl-substituted-8-(3,4-,3- or 4-substituted phenyl) xanthines and the pharmaceutically acceptable salts thereof.

(b) State of the Art

Xanthines of various types have been used or proposed as drugs for various indications. For example theophylline and aminophylline relax the smooth muscle of the bronchial airways and pulmonary blood vessels, thereby acting as pulmonary vasodilators, bronchodilators and smooth muscle relaxants. Like other xanthines these compounds possess the following actions as well: coronary vasodilator, diuretic, cardiac and cerebral stimulant and skeletal muscle stimulant. Dyphylline is another xanthine having activity similar to that of theophylline and aminophylline.

Adenosine is a known vasodilator, negative inotropic and chronotropic agent of the cardiovascular system. Adenosine antagonists such as aminophylline will increase cardiac output which makes them useful as cardiotonic agents. Presently, there are only weak nonselective adenosine antagonists available such as aminophylline and theophylline. The ideal cardiotonic, based on the principle of adenosine antagonism, should reverse the depressed contractility of myocardial muscle caused by endogenously released adenosine without causing an increase in heart rate or peripheral pressure. From that point of view selectivity toward the $A_1$—subclass of adenosine receptor is highly desired.

Presently available xanthine-derivative cardiotonics, theophylline and aminophylline, do not show any remarkable degree of selectivity. The present invention provides new, more potent, selective adenosine antagonists having physical properties, notably increased water solubility, which result in beneficial pharmacological activity.

Synthesized by Bruns et al. (Proc. Nat'l. Acad. Sci. USA, 1983, 80, 2077), 8-arylxanthines show a great increase in the affinity toward the adenosine ($A_1$) receptor with the best compound reported in the series being: 1,3-dipropyl-8-[2-amino-4-chlorophenyl]xanthine [PACPX] (I).

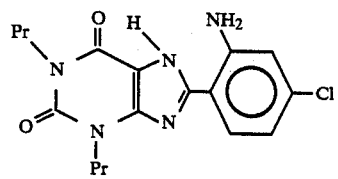

This compound was reported 70,000 times more potent [at the receptor level] than theophylline and selective toward $A_1$—adenosine receptor. It is also approximately 40,000 times more lipophilic. Calculation of its partition coefficient using Rekker's hydrophobic fragmental constants gives an approximate log P=4.0. That fact can be neglected in the studies using isolated receptor preparations since the compound is 70,000 times more potent. However, from the pharmacological point of view the high lipophilicity makes this compound undesirable for therapeutical use. One has to expect an extremely high CNS uptake, poor blood clearance and extensive metabolism. It has been suggested that as an apparent consequence of their extreme lipophilicity, many 8-arylxanthines, such as those disclosed in U.S. Pat. No. 4,593,095, particularly the preferred compound PACPX, demonstrate little overt activity in animals. In one test where activity is seen, The NECA depressed Langendorff heart in guinea pigs, PACPX has unfavorable force and rate properties, whereas the water soluble compounds of this invention increase the force of contraction at doses that are lower than those required.

Bruns attempted to lower the lipophilicity of 8-arylxanthines. He synthesized 8-[4-sulfophenyl]-theophylline (II). This compound was studied at the receptor level by Fredholm and Sandberg (Br. J. Pharmacol. 1983, 80, 639).

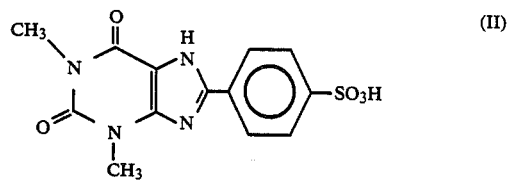

When the above mentioned authors studied the effect of selected xanthine derivatives on the adenosine 5'-ethylcarboxamide (NECA)-induced accumulation of cyclic AMP in guinea pig thymocytes, (II) was only 3 fold less potent than 8-phenyltheophylline while lipophilicity of (II) was two orders of magnitude lower. Unfortunately, introduction of the sulfonyl group led to a decrease in selectivity [Daly et al. J. Med. Chem. 1985, 28, 487].

This invention provides a series of new 8-arylxanthines which retain most of the potency and receptor selectivity of PACPX with simultaneous decrease in the lipophilicity and which cause an increase in the force of contraction in the NECA-depressed Langendorff heart preparation in guinea pigs in doses below those that increase the rate of contraction.

SUMMARY OF THE INVENTION

This invention relates to novel 8-phenylxanthines which are relatively potent adenosine receptor antagonists while being relatively free of side effects. Specifically, this invention provides compounds of the formula:

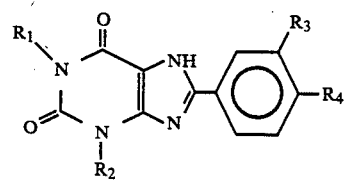

wherein
$R_1$ and $R_2$ are independently selected from alkyls of one to six carbons;
$R_3$ is selected from hydrogen and dimethylaminomethyl and 2,3-dihydroxypropyloxy;

$R_4$ is selected from hydrogen, hydroxy, cyano, —NHCON($R_5$)$_2$, —C(=NH)N($R_5$)$_2$, —NH—C(=NH)N($R_5$)$_2$, wherein each $R_5$ is independently hydrogen or an alkyl group of one to three carbons, with the provisos that (i) when $R_3$ is hydrogen, $R_4$ may not be hydroxy, and (ii) $R_3$ and $R_4$ may not both be hydrogen and pharmaceutically acceptable salts of such compounds. Preferred compounds are those in which $R_1$ and $R_2$ are the same or $R_1$ is n-propyl and $R_2$ is methyl and $R_3$ is hydrogen. Optimally $R_1$ and $R_2$ are both n-propyl. The invention also relates to the use of these compounds as cardiotonic agents.

DETAILED DESCRIPTION OF THE INVENTION

The compounds of the invention are those having the formula:

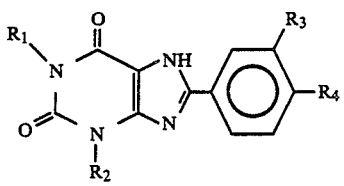

wherein
$R_1$ and $R_2$ are independently selected from alkyls of one to six carbons, preferably methyl or propyl;
$R_3$ is selected from hydrogen and dimethylaminomethyl and 2,3-dihydroxypropyloxy;
$R_4$ is selected from hydroxy, cyano, —NHCON($R_5$)$_2$, —C(=NH)N($R_5$)$_2$, —NH—C(=NH)N($R_5$)$_2$
wherein each $R_5$ is independently hydrogen or an alkyl group of one to three carbons, with the proviso that (i) when $R_3$ is hydrogen, $R_4$ may not be hydroxy and (ii) $R_3$ and $R_4$ may not both be hydrogen, and pharmaceutically acceptable salts of such compounds. Preferred compounds are those in which $R_1$ is n-propyl, $R_2$ is n-propyl or methyl, $R_3$ is hydrogen or dimethylaminomethyl and $R_4$ is hydroxy or —NHCON($R_5$)$_2$. Among the preferred compounds are 1,3-dimethyl-8-(4-ureidophenyl)xanthine; 1,3-dipropyl-8-(4-ureidophenyl)xanthine; 1,3-dipropyl-8-(4-N,N-dimethylureidophenyl)xanthine; 1,3-dipropyl-8-(4-amidinophenyl)xanthine; 1,3-dipropyl-8-(4-cyanophenyl)xanthine, 1,3-dipropyl-8-(3-N,N-dimethylaminomethyl-4-hydroxyphenyl)xanthine, 1-propyl-3-methyl-8-(3-N,N-dimethylaminomethyl-4-hydroxyphenyl)xanthine, 1-propyl-3-methyl-8-(4-cyanophenyl)xanthine, 1,3-dipropyl-8-(4-N-methylamidinophenyl)xanthine, 1,3-dimethyl-8-(4-amidinophenyl)xanthine, 1,3-dimethyl-8-(4-N-methyliminoaminomethylphenyl)xanthine, 1,3-dipropyl-8-(4-guanidinophenyl)xanthine, 1,3-dimethyl-8-(4-guanidinophenyl)xanthine, and 1,3-dipropyl-8-[3-(2,3-dihydroxypropyloxy)phenyl]xanthine.

The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bismethylenesalicyclic, methanesulfonic, ethanedisulfonic, acetic, oxalic, propionic, tartaric, salicyclic, citric, glyconic, aspartic, stearic, palmitic, itaconic, glycolic, p-aminobenzoic, glutamic, benzenesulfonic, hydrochloric, hydrobromic, sulfuric, cyclohexyl sulfamic, phosphoric and nitric acids. Hydrates of the compounds are also included within the invention.

The compounds of the invention provide one or more of the following advantages relative to known 8-arylxanthines:
1. high affinity to adenosine receptor,
2. high selectivity toward $A_1$—adenosine receptor,
3. high water solubility,
4. separation of action resulting in great increase in contractility of adenosine depressed myocardial muscle combined with negligible increase of heart rate and absence of effect on peripheral pressure.

The compounds of the invention have a receptor activity of an order at least that of some prior art compounds having bronchodilating activity. The present compounds should also be useful as bronchodilators. They are also likely to be useful as cardiotonics and possibly as cognitive enhancers. Because certain compounds of the invention are substantially more water soluble than prior art xanthines, it is likely that fewer side effects will be observed since lower doses are likely to lead to clinically effective blood levels.

The compounds would be formulated and used in pharmaceutical compositions typically used with xanthines and other adenosine receptor antagonists. These compositions would contain amounts of the compounds of the invention sufficient to result in delivery to a patient of effective amounts of the compounds. Commonly it is expected that each unit of a given composition will contain 0.01 to 0.5% by weight of the compound. Dosing intervals would depend on the amount of compound administered and the desired blood levels.

The compounds may be synthesized according to known methods. For example synthesis may be effected as follows. 1,3-dipropyl-5,6-diaminouracil may be prepared by standard methods. Condensation of commercially available 1,3-dimethyl-5,6-diaminouracil or 1,3-dipropyl-5,6-diaminouracil with 4-nitrobenzaldehyde yields either 1,3-dimethyl-5-amino-6-(4-nitrophenyl)iminouracil or 1,3-dipropyl-5-amino-6-(4-nitrophenyl)iminouracil. Ring closure may be done by treatment of the iminouracil with diethyl azodicarboxylate (DEAD) or thionyl chloride yielding either 1,3-dimethyl-8-(4-nitrophenyl)xanthine, or 1,3-dipropyl-8-(4-nitrophenyl)xanthine. Catalytic hydrogenation of the 4-nitro group gives 1,3-dimethyl-8-(4-aminophenyl)xanthine or 1,3-dipropyl-8-(4-aminophenyl)xanthine.

Treatment of the foregoing amino derivatives with trichloromethylformate will yield the isocyanates which can be condensed with the desired amine to give 1,3-dipropyl-8-(4-ureidophenyl)xanthine, 1,3-dipropyl-8-(4-N-methylureidophenyl)xanthine, 1,3-dipropyl-8-(4-N,N-dimethylureidophenyl)xanthine, 1,3-dimethyl-8-(4-ureidophenyl)xanthine, 1,3-dimethyl-8-(4-N,N-dimethylureidophenyl)xanthine, and 1,3-dimethyl-8-(4-N-methylureidophenyl)xanthine.

1,3-Dipropyl-8-(4-cyanophenyl)xanthine and 1,3-dimethyl-8-(4-cyanophenyl)xanthine, prepared from the appropriate 1,3-dialkyl-5,6-diaminouracils as described for the related 4-nitrophenyl derivatives, upon treatment with alcoholic HCL will yield the corresponding ethyl imidates which can be treated with the desired amine (NH$_4$OH; CH$_3$NH$_2$; (CH$_3$)$_2$NH) to give 1,3-dipropyl-8-(4-amidinophenyl)xanthine, 1,3-dipropyl-8-(4-N-methylamidinophenyl)xanthine, 1,3-dipropyl-8-(4-N,N-dimethylamidinophenyl)xanthine, 1,3- dimethyl-8-(4-amidinophenyl)xanthine, 1,3-dimethyl-(4-N-methylamidinophenyl)xanthine, and 1,3-dimethyl-(4-N,N-dimethylamidinophenyl)xanthine.

Dehydration of 1,3-dipropyl-8-(4-N-methylureidophenyl)xanthine may be accomplished by treatment with p-toluenesulfonyl chloride in pyridine to give 1,3-dipropyl-8-(4-N-methylcarbodiimidophenyl)xanthine. Condensation of 1,3-dipropyl-8-(4-N-methylcarbodiimidophenyl)xanthine with the desired amine ($CH_3NH_2$; $(CH_3)_2NH$; $NH_4OH$) will give the guanidino derivatives: 1,3-dipropyl-8-(4-N-methylguanidinophenyl)xanthine, 1,3-dipropyl-8-(4-N,N'-dimethylguanidinophenyl)xanthine, and 1,3-dipropyl-8-(4-N-methyl-N'-dimethylguanidinophenyl)xanthine.

1,3-Dipropyl-8-(3-propenyloxyphenyl)xanthine, prepared by treatment of the related 3-hydroxyphenyl derivative with alkyl bromide, was oxidized to afford 1,3-dipropyl-8-[3-(2,3-dihydroxypropyloxy)phenyl]xanthine.

The foregoing is a general description of how to prepare the compounds of this invention. The following examples illustrate the preparation of specific compounds. This however, should not be construed as a limitation of the invention as appropriate variations in the starting materials will produce other compounds set forth herein above.

EXAMPLE 1

1,3-Dipropyl-8-(4-nitrophenyl)xanthine, was prepared by treatment of 1,3-dipropyl-5,6-diaminouracil (1.01 g, 4.5 mmol) with 4-nitrobenzaldehyde (0.85 g, 5.6 mmol) in absolute ethanol (50 ml) in the presence of acetic acid (0.6 ml) and heated at reflux for 1 hour to yield 1,3-dipropyl-5-amino-6-(4-nitrophenyl)iminouracil. Treatment of 1,3-dipropyl-5-amino-6-(4-nitrophenyl)iminouracil (1.2 g, 3.3 mmol) with diethyl azodicarboxylate (7 ml) at 90° C. in toluene (40 ml) gave after dilution with ethanol a precipitate. This precipitate was recrystallized from ethanol yielding 0.95 g of pure product (81%). IR (KBr) 3180 (N—H), 1710(C=O), 1650(C=O), 1520(C=C) cm$^{-1}$; Anal. Calcd. for $C_{17}H_{19}N_5O_4$: MW 357.38: C, 57.14; H, 5.36; N, 19.60. Found: C, 57.22; H, 5.42; N, 19.50.

EXAMPLE 2

1,3-Dipropyl-8-(4-N,N-dimethylureidophenyl) xanthine. 1,3-Dipropyl-8-(4-aminophenyl)xanthine (550 mg, 1.70 mmol), prepared by catalytic ($PtO_2$) hydrogenation of the corresponding 4-nitrophenyl derivative, was treated with trichloromethylformate (TCF) (0.3 ml, 2.5 mmol) in dry dioxane (50 ml) and stirred at room temperature for 20 hours. To this solution dimethylamine (10 ml) was added and refluxed for 5 hours. The solvent was removed under reduced pressure to yield a yellow residue. Repeated recrystallization from ethanol gave pure 1,3-dipropyl-8-(4-N,N-dimethylureidophenyl)xanthine. IR (KBr) 3312 (N—H), 3183 (N—H), 2975 (C—H, alkyl), 1702 (C=O), 1648 (C=O) cm$^{-1}$; $^1$H NMR (DMSO d$_6$) δ8.6-7.5 (m, 6H), 3.9 (m, 4H), 3.0 (s, 6H), 1.8 (m, 4H), 0.9(t, 6H). Anal. Calcd. for $C_{20}H_{26}N_4O_3$, MW. 370.45: C, 60.29; H, 6.58; N, 21.09. Found: C, 59.83, H, 6.71; N, 20.70.

EXAMPLE 3

1,3-Dipropyl-8-(4-cyanophenyl)xanthine was prepared by treatment of 1,3-dipropyl-5,6-diaminouracil (6.37 g, 28.15 mmol) with 4-cyanobenzaldehyde (3.72 g, 28.37 mmol) in absolute ethanol (175 ml) with acetic acid (5 ml) heated at reflux for 2 hours. The reaction mixture was then cooled to 0° C., and the resulting precipitate collected, and recrystallized from ethanol yielding a white solid (8.1 g, 24.0 mmol, 85%) IR (KBr) 3142 (N—H), 2965 (C—H), 2232 (C≡N), 1695 (C=O), 1651 (C=O) cm$^{-1}$; $^1$H NMR (DMSO d$_6$) δ8.2 (d,J=8 Hz, 6H). Anal. Calcd. for $C_{18}H_{19}N_4O_{21}$, MW. 337.38: C, 64.08; H, 5.68; N, 20.76. Found: C, 64.15, H, 5.69; N, 20.72.

EXAMPLE 4

1,3-Dipropyl-8-(4-amidinophenyl)xanthine hydrochloride hemi-hydrate was prepared by treatment of 1,3-dipropyl-8-(4-cyanophenyl)xanthine (4.3 g, 12.7 mmol) with HCl gas (45 minutes) at 0° C. in absolute EtOH (distilled from Mg, 40 ml). The reaction vessel was sealed and allowed to slowly warm to room temperature. After 16 hours, the reaction mixture was diluted with $Et_2O$. The resulting precipitate was collected by filtration and dried under reduced pressure. The crude imidate ester (1.12g, 2.67 mmol) was treated with ammonia gas in ethanol (30 ml) and stirred at room temperature for 8 hours. The solvent was removed under reduced pressure, yielding a white residue. The residue was acidified with HCl and recrystallized from ethanol to yield 650 mg of crude product. Repeated recrystallization from ethanol gave pure product, mp above 300° C. IR (KBr) 3200 (N—H), 3000-2500 br, 1710 (C=O), 1700 (C=N), 1650 (C=O) cm$^{-1}$; $^1$H NMR (DMSO d$_6$) δ8.5(d,2H), 8.2(d,2H), 7.2-8.0(m,4H), 4.2(q,4H), 1.8(m,4H), 0.9(t,6H); Anal. Calcd. for $C_{18}H_{22}N_6O_2 \cdot HCL \cdot 0.5H_2O$, MW. 399.8: C, 54.07; H, 6.05; N, 21.02; Cl, 8.87. Found: C, 54.06; H, 5.92; N, 21.32; Cl 8.92.

EXAMPLE 5

1,3-Dipropyl-8-(4-N-methylamidinophenyl)xanthine hydrochloride hydrate was prepared by treatment of 1,3-dipropyl-8-(4-cyanophenyl)xanthine (4.3g, 12.7 mmol) with HCl gas (45 minutes) at 0° C. in absolute ethanol (distilled from Mg, 40 ml). The reaction vessel was sealed and allowed to slowly warm to room temperature. After 16 hours the reaction mixture was diluted with ether. The resulting precipitate was collected by filtration and dried under reduced pressure. The crude imidate ester (1.72 g, 4.10 mmol) was treated with aqueous methylamine (40%, 3 ml) in ethanol (30 ml) and stirred at room temperature for 2 hours. The solvent was removed under reduced pressure to yield a pale yellow residue. The residue was acidified and recrystallized from EtOH, further recrystallization from ethanol gave pure product. mp. above 300° C.; IR (KBr) 3104 (N—H), 2965 (C—H) 2877 (C—H), 1702 (C=O), 1661 (C=O) cm$^{-1}$; $^1$H NMR (DMSO d$_6$) δ8.3(d, J=8 Hz, 2H), 8.0 (d, J=8 Hz,2H), 4.2(m,4H), 3.3(s,3H), 1.8(m,4H), 0.9(t,6H); Anal. Calcd. for $C_{19}H_{25}N_6O_2 \cdot HCl \cdot H_2O$, MW. 410.89: C, 53.96; H, 6.44; N, 19.87; Cl, 8.38. Found: C, 53.75; H, 6.49; N, 20.31; Cl 8.59.

EXAMPLE 6

1,3-Dipropyl-8-(4-carboethoxyphenyl)xanthine was obtained as a major by-product in the syntheses of both 1,3-dipropyl-8-(4-N-methylamidinophenyl)xanthine hydrochloride hydrate and 1,3-dipropyl-8-(4-amidinophenyl)xanthine hydrochloride hydrate. mp. 286°-287° C.; IR (KBr) 3173 (N—H) 2970 (C—H), 1704 (C=O), 1663 (C=O) cm$^{-1}$; H NMR (DMSO d$_6$) δ8.2(m,4H), 4.3(t,2H), 3.9(m,4H), 1.5(m,7H), 0.9(t,6H); Anal. Calcd. for $C_{20}H_{24}N_4O_4$ MW. 384.43: C,62.49; H, 6.29; N, 14.57. Found: C, 62.29; H, 6.34; N, 14.49.

EXAMPLE 7

6-Amino-1-methyl-5-nitroso-3-n-propyluracil. 6-Amino-1-methyl-3-n-propyluracil (13.2 g, 7.3 mmol) was dissolved in 10–15 ml of acetic acid and the solution was warmed on a hot plate to 60°–70° C. Then, with stirring, a solution of sodium nitrite (5.3 g, 7.7 mmol) in 100 ml of water was added in 10 ml portions over 10 minutes. A brownish-purple precipitate formed. The reaction mixture was cooled to 10° C. and the precipitate was collected by vacuum filtration, washed with 10 ml of acetone, and air-dried to give 8.3 g (55%) of 6-amino-1-methyl-5-nitroso-3-n-propyluracil as a purple solid. $^1$H NMR (DMSO-d$_6$+D$_2$O) $\delta$0.90 (t, J=7 Hz, 3 H), 1.62 (sextet, J=7 Hz, 2 H), 3.26 (s, 3 H), 3.87 (t, J=7 Hz, 2 H).

EXAMPLE 8

5,6-Diamino-1-methyl-3-n-propyluracil. 6-Amino-1-methyl-5-nitroso-3-n-propyluracil (8.3 g, 40 mmol) was slurried with 75 ml of absolute ethanol and 100 mg of 10% Pd/C. The mixture was placed in a Parr bomb that was then pressurized to 80 psi with hydrogen. The bomb was repressurized as needed. After 2 hours, no further uptake of hydrogen was observed. The reaction mixture was filtered to give ca. 1.6 g of starting material. The solvent was removed from the greenish mother liquors by rotary evaporation to give a greenish-yellow solid. Trituration of the solid with ca. 25 ml of methanol gave an off-white solid which was collected by vacuum filtration, washed with methanol (3×5 ml) and ether (3×10 ml), and air-dried to give 4.4 g (70% based on recovered starting material) of 5,6-diamino-1-methyl-3-n-propyluracil which was used directly in the next step.

EXAMPLE 9

8-(4-Cyanophenyl)-3-methyl-1-n-propylxanthine. A mixture of 5,6-diamino-1-methyl-3-n-propyluracil (6.00 g, 30.3 mmol), 4-cyanobenzaldehyde (3.97 g, 30.3 mmol), and 1.0 ml of acetic acid of 100 ml of EtOH was brought to reflux. A precipitate began forming immediately. The mixture was refluxed overnight and then cooled to rt. The precipitate was collected by vacuum filtration, washed with ether, and air-dried to give 8.77 g (93%) of the imine as a yellow solid that was used without further purification. $^1$H NMR (DMSO-d$_6$) $\delta$0.85 (t, J=7.5 Hz, 3 H), 1.53 (sextet, J=7.5 Hz, 2 H), 3.40 (s, 3 H), 3.77 (t, J=7.5 Hz, 2 H), 7.83 (d, J=7.8 Hz, 2 H), 8.11 (d, J=7.8 Hz, 2 H), 9.76 (s, 1 H).

The imine (8.95 g, 28.8 mmol) was suspended in 200 ml of glyme and the mixture was brought to reflux. Some imine remained undissolved. DIAD (8.7 g, 8.5 ml, 43.2 mmol) was added through the condenser. Within 10 minutes everything had dissolved. After 1.5 hours, precipitate began forming. Reflux was continued for an additional 30 minutes. The precipitate was collected by vacuum filtration and the filter cake was washed with glyme (3×25 ml) and ether (3×25 ml) and recrystallized from EtOH to give 7.97 g (90%) of the xanthine. mp 314°–318° C.; IR (KBr) 3180, 229, 1692, 1653 cm$^{-1}$; $^1$H NMR (DMSO-d$_6$) $\delta$0.88 (t, J=7.5 Hz, 3 H), 1.58 (sextet, J=7.5 Hz, 2 H), 3.50 (s, 3 H), 3.86 (t, J=7.5 Hz, 2 H), 7.99 (d, J=8.1 Hz, 2 H), 8.28 (d, J=8.1 Hz, 2 H). Anal. Calcd. for $C_{16}H_{15}N_5O_2$: C, 62.13; H, 4.89; N, 22.64. Found: C, 61.99; H, 4.90; N, 22.56. TLC - silica; ether:hexane, 75:25; blue fluorescence under UV; Rf=0.5.

EXAMPLE 10

6-Amino-3-methyl-5-nitroso-1-n-propyluracil. 6-Amino-3-methyl-1-n-propyluracil (10.46 g, 57.8 mmol) was dissolved in 10 ml of acetic acid at 90° C. Then, with stirring, a solution of sodium nitrite (4.19 g, 60.8 mmol) in 100 ml of water was added in 10 ml portions over 5 minutes. A purple color formed immediately followed by a purple precipitate. The mixture was cooled in the freezer for 20 minutes and then the precipitate was collected by vacuum filtration, washed with water (2×30 ml) and acetone (2×10 ml), and air-dried to give 6-amino-3-methyl-5-nitroso-1-n-propyluracil as purple needles (10.02 g, 83%). $^1$H NMR (DMSO-d$_6$+D$_2$O) $\delta$0.89 (t, J=8 Hz, 3 H), 1.55 (sextet, J=8 Hz, 2 H), 3.27 (s, 3 H), 3.80 (t, J=8 Hz, 2 H).

EXAMPLE 11

5,6-Diamino-3-methyl-1-n-propyluracil. 6-Amino-3-methyl-5-nitroso-1-n-propyluracil (11.53 g, 54.9 mmol) was slurried with 75 ml of anhydrous ethanol and 200 mg of 20% Pd/C in a Parr bomb. The bomb was pressurized to 80 psi with hydrogen and repressurized as needed during the reaction. After 2.5 hours, no further uptake of hydrogen was observed. The reaction solution was filtered through celite. The solvent was removed by rotary evaporation to give a yellowish solid which was triturated with ethanol:ether (1:1; 100 ml) to give an off-white solid that was collected by vacuum filtration, washed with ethanol:ether (1:1; 2×10 ml) and ether (2×25 ml), and air-dried to give 5,6-diamino-3-methyl-2-n-propyluracil (6.17, 57%) that was used directly in the next step.

EXAMPLE 12

6-Amino-3-methyl-5-(4-cyanophenyl)imino-1-n-propyluracil. 5,6-Diamino-3-methyl-1-n-propyluracil (6.17 g, 32 mmol) is mixed with 85 ml anhydrous ethanol, 7 ml acetic acid, and 3.5 ml (34 mmol) of 4-cyanobenzaldehyde. The mixture is refluxed overnight. The reaction mixture is then concentrated to 30 ml by rotary evaporation and then dissolved in 500 ml of ether. The solution is washed with water (3×50 ml), 0.1 M potassium carbonate (3×100 ml), and then dried over sodium sulfate. Removal of the solvent gives 6-amino-3-methyl-5-(4-cyanophenyl)imido-1-n-propyluracil.

EXAMPLE 13

1-Methyl-8-(4-cyanophenyl)-3-n-propylxanthine. 6-Amino-3-methyl-5-(4-cyanophenyl)imino-1-n-propyluracil (5.00 g, 17.4 mmol) is dissolved in 75 ml of glyme and 4.2 ml (21.4 mmol) of diisopropylazodicarboxylate is added. The solution is then brought to reflux. The solution is refluxed 30 minutes and then filtered hot. The filter cake is washed with glyme (3×20 ml) and ether (3×30 ml) and airdried to give 1-methyl-8-(4-cyanophenyl)-3-n-propylxanthine.

EXAMPLE 14

1,3-Dimethyl-8-(4-cyanophenyl)xanthine hydrate was prepared by treatment of 1,3-dimethyl-5,6-diaminouracil hydrate (9.0 g, 52.9 mmol) with 4-cyanobenzaldehyde (6.9 g, 52.7 mmol) in ethanol (700 ml) in the presence of acetic acid (3 ml) at reflux for 5 hours. The reaction mixture was cooled to 0° C. and the resulting precipitate was collected. The crude iminouracil was dissolved in ethylene glycol dimethyl ether (700 ml) and treated with DEAD (11 ml) at reflux for 4 hours. The reaction mixture was cooled to 0° C. and the resulting precipitate was collected and recrystallized from 4:4:2 methanol:ethyl acetate:water. mp.>300° C. IR (KBr) 3412, 3320, 2965, 2936, 2877, 1680, 1604, 1512 cm$^{-1}$. Anal. Calcd. for $C_{14}H_{11}N_5O_2 \cdot H_2O$. C,56.18, H, 4.37; N, 23.40. Found: C, 56.20; H, 4.04; N,23.17.

EXAMPLE 15

1,3-Dimethyl-8-(4-N-methylamidinophenyl)xanthine hydrochloride hydrate was prepared by treatment of 1,3-dimethyl-8-(4-cyanophenyl)xanthine (12.2g, 43.3 mmol) with ethanolic HCl and stirred at room temperature for 10 days. The reaction mixture was cooled and the resulting precipitate was collected and degassed under vacuum. The crude imidate (15.5 g, 42.7 mmol) was treated with ethanolic methylamine for 5 days. After the reaction mixture was cooled the precipitate was collected and acidified with HCl and recrystallized from ethanol. mp>300° C. IR (KBr) 3530, 3096, 2977, 1707, 1669, 1640, 1579, 1561, 1422 cm$^{-1}$. Anal. Calcd. for $C_{15}H_{17}N_6O \cdot HCl \cdot H_2O$: C, 47.94; H, 5.36; N, 22.36; Cl, 9.43. Found: C, 47.81; H, 5.37; N, 22.30; Cl, 9.43.

EXAMPLE 16

1,3-Dipropyl-8-(4-aminomethylphenyl)xanthine hydrochloride hydrate was prepared by reduction of 1,3-dipropyl-8-(4-cyanophenyl)xanthine (1.5 g, 4.4 mmol) with Pd/C 10% (50 mg) at 80 psi of hydrogen at 50° C. for 7 hours. The product was recrystallized from ethanol. mp.>300° C. IR (KBr) 3337, 3098, 2954, 1707, 1658, 1532 cm$^{-1}$. $^1$H NMR (DMSO-d$_6$) δ0.9 (t, 6 H), 1.7 (m, 4H), 3.9 (m, 4 H), 4.1 (s, 2 H), 7.6 (d, 7 Hz, 2 H), 8.2 (d, 7 Hz, 2 H). Anal. Calcd. for $C_{18}H_{23}N_5O_2 \cdot HCl \cdot H_2O$: C, 54.94; H, 6.17; N, 17.70; Cl, 9.10. Found: C, 54.61; H, 6.62; N, 17.69; Cl, 8.96.

EXAMPLE 17

1,3-Dimethyl-8-(4-amidinophenyl)xanthine hydrochloride hydrate was prepared by treatment of 1,3-dimethyl-8-(4-cyanophenyl)xanthine (6.0 g, 21.4 mmol) with HCl gas in anhydrous ethanol (2 l) for 4 hours. The reaction mixture was stirred at room temperature for 2 days. The resulting precipitate was collected and dried under reduced pressure for 3 days. The imidate (7.37 g) was dissolved in anhydrous ethanol (2l) and was treated with ammonia gas for 15 minutes. The reaction mixture was stirred at room temperature for 2 days. The resulting precipitate was collected by filtration and dried under reduced pressure, yielding 6.4 g (19 mmol 80%) of product. mp>300° C. IR (KBr) 3140, 3047, 1702, 1653, 1648, 1543, 1468 cm$^{-1}$; $^1$H NMR (80 Hz) (DMSO-d$_6$) 3.29 (s, 3 H), 3.53 (s, 3 H), 7.98 (d, J=9 Hz, 2 H), 8.34 (d, J=9 Hz, 2 H), 9.4 (d). Anal. Calcd. for $C_{14}H_{14}N_6O_3$ HCl·H$_2$O: C, 47.67; H, 4.86; N, 23.82; Cl, 10.05. Found: C, 47.48; H, 4.91; N, 23.64; Cl, 9.98.

EXAMPLE 18

1,3-Dipropyl-8-(3-N,N-dimethylaminomethyl-4hydroxyphenyl)xanthine hydrochloride hydrate was prepared by the treatment of 1,3-dipropyl-5,6-diaminouracil (6.5 g, 28.8 mmol) with 3-N,N-dimethyl-4-hydroxybenzaldehyde (6 g) in ethanol (100 ml) in the presence of acetic acid (0.5 ml). The reaction mixture was heated at reflux for 10 hours. The ethanol was removed under reduced pressure. The resulting crude product was dissolved in toluene (100 ml) and treated with DEAD (5 ml) at 80° C. for 6 hours. The toluene was removed under pressure. To isolate the desired product, the crude reaction mixture was subjected to chromatography (flash, prep HPLC, etc.). The product was acidified with HCl to form the hydrochloride salt, mp 208°-210° C. IR (KBr) 3412, 3085, 2965, 1705, 1661, 1565, 1483, 1448, 1370, 1283, 1263 cm$^{-1}$. $^1$H NMR (300 Hz) (CD$_3$OD) 0.88 (m, 6 H), 1.53 (q, J=7 Hz, 2 H), 1.68 (q, J=7 Hz, 2 H), 2.77 (s, 6 H), 4.26 (s, 2 H), 3.82 (t, J=7.5 Hz, 2 H), 3.98 (t, J=7.5 Hz, 2 H), 6.95 (d, J=8.5 Hz, 1 H), 7.88 (dd, J=6, 2 Hz, 1 H), 7.95 (d, J=2 Hz, 1 H). $^{13}$C NMR (75 Hz) (DMSO-d$_6$). 10.86, 11.03, 20.81, 42.31, 44.53, 48.53, 55.46, 115.94, 117.20, 129.95, 119.94, 131.30, 150.83, 154.03, 158.27 ppm. Anal. Calcd. for $C_{20}H_{27}N_5O_3 \cdot HCl \cdot H_2O$: C, 54.60; H, 6.78; N, 15.91; Cl, 8.05. Found: C, 55.00; H,7.12; N, 15.08; Cl, 7.66.

EXAMPLE 19

1,3-Dipropyl-8-(4-guanidinomethylphenyl)xanthine hydrochloride was prepared by treatment of 1,3-dipropyl-8-(4-aminomethylphenyl)xanthine (150 mg, 0.44 mmol) with S-methylthiouronium iodide (250 mg, 1.2 mmol) in refluxing 9:1 ethylene glycol monomethyl ether/water (100 ml) for 48 hours. The reaction mixture was cooled to 0° C. and the crude product was collected by filtration. This material was dissolved in EtOH and treated with HCl, the solvent was then removed under reduced pressure. This procedure was repeated three times. The product was recrystallized from EtOH. mp. >250° C.; IR (KBr) 3451, 3343, 3187, 2973, 2876, 1700, 1654, 1482 cm$-1$; $^1$H NMR (300 MHz, DMSO) δ8.05(d,2H), 7.37(d,2H), 4.27(s,2H), 4.03(t, 2H), 3.88(t,2H), 1.74(q,2H), 1.58(q,2H), 0.91(dt,6H); $^{13}$C NMR (75 MHz, DMSO) 158.95, 154.26, 150.90, 150.14, 148.54, 143.72, 127.66, 127.24, 126.64, 107.80, 44.64, 42.37, 21.10, 11.43, 11.30 ppm.

EXAMPLE 20

1,3-Dipropyl-8-[3-(2,3-dihydroxypropyloxy)-phenyl]xanthine was prepared by stirring a solution of 0.42 g (1.1 mmole) of 1,3-dipropyl-8-(3-propenyloxyphenyl)xanthine, obtained by etherification of the corresponding hydroxyphenyl derivative with alkyl bromide in the presence of base, in 50 ml of methylene chloride with 10 ml of a saturated aqueous solution of potassium permanganate in the presence of 0.2 g of tricaprylmethyl-ammonium chloride for 36 hours at room temperature. Excess potassium permanganate was removed by washing with water. The organic phase was separated, dried, filtered through celite and concentrated to give a yellow solid. This material was purified by preparative HPLC using a reverse phase C-18 column, eluting with aqueous methanol to give nearly colorless crystals, mp >250° C. $^1$H-NMR (DMSO-d$_6$, 300 MHz) δ7.78 (s, 1H), 7.75 (s, 1H), 7.4 (t, 1H), 7.05 (d, 1H) , 5.0 (d, 1H), 4.7 (t, 1H), 4.0 (m, 7H), 3.5 (t, 2H), 1.78 (q, 2H), 1.5 (q, 2H), 0.9 (m, 6H). Anal. Calcd. for $C_{20}H_{26}N_4O_5$: M.W. 402.450: C,59.68; H, 6.51; N, 13.92. Found: C, 59.56; H, 6.55; N, 13.87

The following examples contain tests which reflect the potency of the compounds of the invention as adenosine receptor antagonists.

EXAMPLE 21

Adenosine Receptor Binding Assay. The potency of 8-arylxanthine compounds to inhibit the specific binding of [³H]-cyclohexyladenosine ([³H]CHA) to adenosine receptor sites on guinea pig cortical membranes was examined using standard in vitro ligand binding techniques. The assay protocol utilized in these studies is a slight modification of the methods described by Bruns et al. (Proc. Natl. Acad. Sci. 77: 5547, 1980) and Williams et al. (Neurosci. Lett. 35:46, 1983). Briefly, guinea pig cortical tissue was homogenized in ice cold 50 mM Tris HCl buffer (pH 7.4) using a Brinkman Polytron. The homogenate was centrifuged at 48,000 x g for 10 minutes and the resulting tissue pellet was suspended in fresh cold buffer to yield a tissue concentration of 10 mg (wet weight)/ml. This tissue suspension was incubated for 30 minutes at 37° C. in the presence of adenosine deaminase (0.2 I.U./mg tissue). Following this incubation, the tissue suspension was centrifuged as before and the resulting pellet was suspended in fresh buffer at a concentration of 7–10 mg tissue (wet weight)/ml. Inhibition of the specific binding of [³H]CHA (New England Nuclear; 25 Ci/mmol) was examined in a total volume of 2 ml containing 50 mM Tris HCl, 7–10 mg of cortical tissue (1 ml of tissue suspension), 4 nM [³H]CHA and various concentrations of the test compounds. Nonspecific binding was determined in the presence of $10^{-5}$M 2-chloroadenosine. The binding reaction was carried out for 120 minutes at 23° C. and was terminated by vacuum filtration over Whatman GF/B filters using a Brandel M-48R Cell Harvester. The filters were washed 3 times with 3 ml of cold buffer and placed in scintillation vials in a Beckman LS 3801 scintillation counter. Dose-inhibition curves were generated with 10–12 concentrations of the test compound using triplicate incubations. The inhibition constants (Ki value) were calculated using EBDA, a log-logit iterative curve fitting program (McPhearson, Comput. Prog. Biomed. 107:220, 1983). Results of this test are set forth in the Table.

EXAMPLE 22

Adenosine Receptor Linked Adenylate Cyclase. The $A_2$ receptor mediated stimulation of adenylate cyclase was measured by a modification of the procedure of Premont et al. (Molec. Pharmacol. 16: 790, 1979). Typically, pheochromocytoma cell (PC12) membranes were thawed and added to a reaction mixture containing a final concentration of 25 mM Tris-HCl, pH 7.1, 1 mM MgCl$_2$, 50 μM ATP, 50 μM cAMP, 0.1 mM papaverine, 0.4 IU/ml adenosine deaminase, 5 mM creatine phosphate, 0.2 mg/ml creatine phosphokinase, 10 μg membrane protein, [α³²P]ATP (μ10⁻⁶DPM), 5 μM GTP, and various concentrations of adenosine agonists and/or antagonists in a final volume of 100 μl. The reaction was initiated with the addition of tissue and incubated 30° C. for 20 minutes. Reactions were terminated with 100 μl of 40 mM ATP, 1.4 mM cAMP and 2% SDS. ³²P-cAMP isolated according to the procedure to the procedure of Salomon et al. (Adv. Cyclic Nucleotide Res. 10: 35, 1979).

The $A_1$ receptor mediated inhibition of adenylate cyclase activity was measured by a modification of the procedure of Londos et al. (Proc. Natl. Acad. Sci. 75: 5362, 1978). Membrane protein (10–15 μg) was added to a reaction mixture containing a final concentration of 25 mM Tris-HCl (pH 7.4), 2 mM MgCl$_2$ 50 μM ATP, 50 μM cAMP, 1 mM dithiothreitol, 0.25 mg/ml BSA, 1 IU/ml adenosine deaminase, 5 mM creatine phosphate, 0.2 mg/ml creatine phosphokinase, 80 mM NaCl, [α³²P]ATP (1.5 c 10⁻⁶DPM) and 100M GTP in 100 μl final volume. Incubations were carried out for 10 minutes at 24° C. Reactions were terminated and the ³²P-cAMP was isolated in an identical manner to that described above.

The Ki values for the test compounds were derived from Schild analysis as described by Tallarida et al. (Life Sciences 25: 637, 1979) in which the progressive shift in the dose response to a standard agonist was assessed using 3 concentrations of the test compound distributed over a 100-fold molar range. All incubations were performed in triplicate. Results are set forth in the Table.

EXAMPLE 23

NECA Depressed Langendorff Heart. Hearts were rapidly excised from male guinea-pigs and transferred to a beaker containing a Krebs-bicarbonate solution at 5° C. Each heart was gently massaged to clear it of blood and clots, and the surrounding tissue was cut away. The cut aortic stump was secured to a glass cannula for retrograde perfusion of the coronary circulation.

Perfusion was at a constant rate of 5–7 ml/min, produced with a Holter peristaltic pump. The Krebs-bicarbonate solution (NaCl, 118.4; KCl, 4.7; CaCl$_2$-2H$_2$O, 1.9; NaHCO$_3$, 25; MgSO$_4$-7H$_2$O, 1.2; glucose, 11.7; NaH$_2$PO$_4$-2H$_2$O, 1.2; EDTA, 2 mmole/liter) was gassed with 95% O$_2$/5% CO$_2$ before being passed into the pump, warming coils (33° C.) and aortic cannula. Alterations in perfusion pressure arising from changes in coronary vascular resistance were recorded on a Gould recorder by means of Gould pressure transducers attached at a sidearm of the aortic cannula. Isometric contractions of the heart were recorded with a Grass transducer attached by a suture via a pulley to a clip on the apex of the ventricles. Rates of contraction were determined by counting heart beats.

Drugs were added directly into the perfusion solutions. Drug concentrations were changed by switching solutions. Cardiac functions were depressed with NECA or adenosine by infusing a solution of one or the other (011–025 μg/min) into the perfusion solution through an injection port located immediately adjacent to the warming coil. Results of the tests are reported in The Table. IC$_{50}$ is defined as the concentration of compound that will cause 50 percent inhibition of the NECA-induced depression of force and rate of an isolated guinea pig heart. In the Table the compounds tested have the following formula:

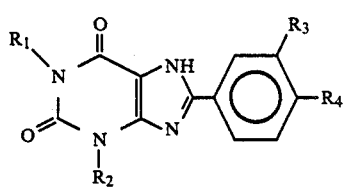

TABLE

Solubility and biochemical properties of 8-arylxanthines

| $R_1$ | $R_2$ | $R_3$ | $R_4$ | Solubility (mg/ml) 37° C. (Salt) | $[^3H]$—CHA Ki nM | Adenylate cyclase $A_1$ Ki nM | $A_2$ Ki nM | $A_2/A_1$ | NECA - Depressed Langendorff Heart (Guinea Pig) $TC_{50}$ (uM) Force | Rate | Force/Rate |
|---|---|---|---|---|---|---|---|---|---|---|---|
| Pr | Pr | (2-$NH_2$) | Cl(PACPX) | <0.0004 | 45 | 12.6 | 421 | 33.4 | 1.11 | 0.18 | 6.17 |
| Me | Me | H | C(NH)$NH_2$ | — | 1139 | 244 | 523 | 2.1 | 2.01 | 15.6 | 0.13 |
| Me | Me | H | C(NH)NHMe | — | 1845 | — | — | — | 3.64 | 18.4 | 0.20 |
| Pr | Pr | H | $CH_2NH_2$ | 0.5 | 66.8 | 16.3 | 432 | 26 | 0.57 | 2.0 | 0.28 |
| Pr | Pr | $CH_2NMe_2$ | OH | 25.0 | 169 | 88.7 | 664 | 7 | 1.49 | 2.06 | 0.72 |
| Pr | Pr | H | COOEt | — | 423 | 26.9 | 529 | 20 | 4.78 | 7.84 | 0.61 |
| Pr | Pr | H | C(NH)$NH_2$ | 3.0 | 81 | 9.7 | 309 | 31.9 | 1.40 | 7.03 | 0.20 |
| Pr | Pr | H | C(NH)NHMe | 1.0 | 129 | 12.0 | 140 | 11.7 | 1.47 | 3.77 | 0.39 |
| Pr | Pr | H | NHC(=O)$NMe_2$ | 0.08 | 86 | — | 131 | — | 0.36 | 0.98 | 0.61 |
| Pr | Pr | $OCH_2(CH_2OH)_2$ | H | 0.25 | — | — | — | — | 0.49 | 1.04 | 0.47 |

— = Not determined.

What is claimed is:

1. A compound of the formula

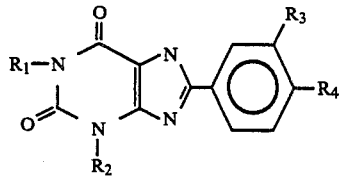

wherein
$R_1$ and $R_2$ are independently selected from alkyls of one to six carbons;
$R_3$ is selected from hydrogen, dimethylaminomethyl and 2,3-dihydroxypropyloxy;
$R_4$ is selected from hydroxy, cyano, —NHCON($R_5$)$_2$, —C(=NH)N($R_5$)$_2$, and —NHC(=NH)N($R_5$)$_2$, wherein each $R_5$ is independently hydrogen or an alkyl group of one to three carbons, with the provisos that when $R_3$ is hydrogen, $R_4$ may not be hydroxy, when $R_3$ is dimethylaminomethyl, $R_4$ is hydroxy and when $R_3$ is 2,3-dihydoxypropyloxy, $R_4$ is hydrogen
and pharmaceutically acceptable salts of such compounds.

2. The compound of claim 1 wherein $R_1$ and $R_2$ are propyl.

3. The compound of claim 1 wherein $R_1$ and $R_2$ are n-propyl, $R_3$ is hydrogen and $R_4$ is —NHCON($R_5$)$_2$.

4. The compound of claim 1 wherein $R_1$ and $R_2$ are n-propyl, $R_3$ is hydrogen and $R_4$ is C(=NH)N($R_5$)$_2$.

5. The compound of claim 1 wherein $R_1$ and $R_2$ are not the same and are selected from n-propyl and methyl.

6. The compound of claim 1 wherein $R_1$ and $R_2$ are n-propyl, $R_3$ is hydrogen and $R_4$ is selected from cyano, —NHCON($R_5$)$_2$, —C(=NH)N($R_5$)$_2$ and —NHC(=NH)N($R_5$)$_2$.

7. The compound of claim 1 wherein $R_1$ and $R_2$ are n-propyl and $R_3$ is 2,3-dihydroxypropyloxy.

8. The compound of claim 1 wherein $R_1$ and $R_2$ are n-propyl, $R_3$ is dimethylaminomethyl and $R_4$ is hydroxy.

* * * * *